United States Patent [19]

Alexander

[11] Patent Number: 4,495,180

[45] Date of Patent: Jan. 22, 1985

[54] PRODRUGS OF ARA-A AN ANTIVIRAL AGENT

[75] Inventor: Jose Alexander, Lawrence, Kans.

[73] Assignee: Merck & Co., Inc., Rahway, N.J.

[21] Appl. No.: 390,444

[22] Filed: Jun. 21, 1982

[51] Int. Cl.³ .................. A61K 31/70; C07H 19/06
[52] U.S. Cl. ................................. 514/46; 536/26
[58] Field of Search ..................... 536/26; 424/180

[56] References Cited

U.S. PATENT DOCUMENTS 3,551,409  12/1970  Kampe et al. ..................... 536/26
3,787,391  1/1974   Jahn et al. ........................ 536/26
3,901,876  8/1975   Vorbrüggen et al. ............. 536/26
4,388,308  6/1983   Hamilton et al. .................. 536/26

*Primary Examiner*—Ethel G. Love
*Attorney, Agent, or Firm*—R. Brent Olson; Michael C. Sudol, Jr.; Mario A. Monaco

[57] ABSTRACT

This invention relates to new organic compounds that are prodrugs of the antiviral agent Ara-A which is 9-($\beta$-D-arabinofuranosyl)adenine. These compounds by virtue of their high lipid solubility will penetrate the stratum cornium and on entry the enzymatic cleavage will regenerate the antiviral compound Ara-A.

9 Claims, No Drawings

PRODRUGS OF ARA-A AN ANTIVIRAL AGENT

BACKGROUND OF THE INVENTION

The present invention relates to novel and useful derivatives of the antiviral agent Ara-A. In particular the invention relates to novel prodrug forms which are low melting, lipid soluble and permeable through topical membranes such as skin, ophthalmic membranes and the like.

For the purpose of this specification, the term "prodrug" denotes a derivative of a known and proven prior art antiviral compound which derivative when administered to warm blooded animals cleaves in such a manner as to release the proven drug form at its target site of activity. The enzymatic and/or chemical hydrolytic cleavage of the compounds of the present invention occurs in such a manner that the proven drug from (Ara-A) is released and permits the same to attain a higher bioavailability leve than that which could be obtained if the proven drug form per se was administered. The cleaved moiety is metabolized to nontoxic metabolic products.

Ara-A is an antimetabolite with a very high therapeutic index that is effective when used systemically against herpes zoster infections in immuno-suppressed patients and patients with herpes simplex encephalitis. It is also effective topically against herpes simplex keratitis of the eye when used as the monophosphate. Despite its efficacy, its low aqueous solubility, (0.4 mg/ml) at 25° and poor lipophilicity precludes its use as a topical agent for treating genital, oral and other cutaneous herpes infections. It is believed that between 20 and 45 percent of the United States population are affected by recurrent herpes simplex labialis. A recent double-blind radomized study with 233 patients with topical Ara-A monophosphate proved its ineffectiveness because of the failure of the drug to penetrate the skin and reach the infected cells to inhibit viral replication [New England J. Med. 300, 1180 (1979)]. In vitro drug diffusion studies in human vaginal mucosa and foreskin showed minimal penetration of the drug across the skin. But in the hairless mouse model of herpes simplex skin infection, increasing the skin penetration of the drug by iontophoresis enhanced efficacy. It is also known the derivatization of the 5'-hydroxyl group of Ara-A inhibits deamination of the adenine nucleus by adenosine deaminase to give 9-$\beta$-D-arabinofuranosylhypoxanthine the major metabolite which has little antiviral activity.

Thus there exists a clear and present need for novel latentiated forms of Ara-A, which derivatives would be conspicuously devoid of those disadvantages and drawbacks that to date have characterized the prior art compounds.

The object of the present invention is to provide suitable prodrugs of Ara-A with greater lipophilicity and hence increased potential for biomembrane transport and in addition, resistance to adenosine deaminase, the enzyme responsible for metabolic deactivation.

Derivatization of Ara-A has been accomplished before, but this consists mostly of esterification of the hydroxyl group(s) of the arabinose residue and irreversible acylation or alkylation of N-1 and/or $N^6$ of the adenine moiety (T. H. Haskell, *Ana. N.Y. Acad. Sci.*, 284, 81 (1977) and U.S. Pat. Nos. 3,651,045; 4,048,432; 4,055,718 and 4,055,717).

Though the reaction of nucleosides with formaldehyde has been studied extensively during the last three decades, the addition product of formaldehyde to aminopurines and especially to the adenine moiety of the nucleosides in aqueous solutions has never be isolated and characterized (D. M. Brown "Reactions of Polynucleotides and Nucleic Acids" in *Basic Principles of Nucleic Acid Chemistry*, Ed., P. O. P. Tso, Vol. II, p. 24, Academic Press, 1974).

DETAILED DESCRIPTION OF THE INVENTION

The present invention relates to novel and useful derivatives of the antiviral agent Ara-A. In particular the invention relates to novel prodrug forms which are low-melting, lipid soluble and permeable through topical membranes such as skin, ophthalmic membranes and the like.

The novel prodrug forms of the antiviral agent 9-($\beta$-D-arabinofuranosyl)adenine have the formula:

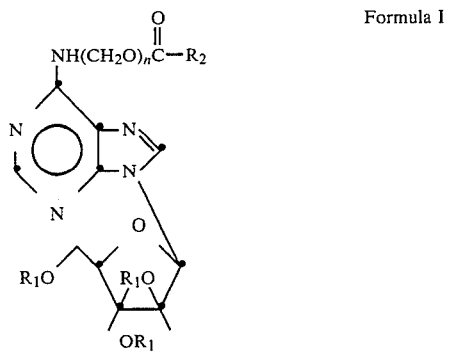

Formula I wherein
n is 1 or 2;
$R_1$ is independently H or lower alkanoyl having from 1 to 4 carbon atom such as acetyl;
$R_2$ is selected from the group consisting of:
(a) straight or branched chain alkyl having from 1–20 carbon atoms such as methyl, isopropyl, t-butyl, n-pentyl and the like;
(b) aryl having from 6–10 carbon atoms particularly phenyl;
(c) cycloalkyl having from 3–8 carbon atoms such as cyclohexyl;
(d) alkenyl having from 2–20 carbon atoms such as hexenyl;
(e) cycloalkenyl having from 4–8 carbon atoms such as cyclohexenyl;
(f) alkynyl having from 2 to 20 carbon atoms such as propargyl;
(g) aralkyl having from 7–26 carbon atoms such as benzyl;
(h) aralkenyl having from 7–26 carbon atoms such as styryl;
(i) lower acyloxy alkyl having from 2–20 carbon atoms as acetoxymethyl;
(j) carboxyalkyl having from 2–20 carbon atoms such as ethoxycarbonyl ethyl;
(k) saturated or unsaturated monoheterocyclic or polyheterocyclic or fused heterocyclic structure containing from 1–3 of any one of the heteroatoms N, S or O in each heterocyclic ring thereof and each of said rings being from 3–8 membered such as piperidine, thiophene and furan;
(l) saturated or unsaturated mono- or polysubstituted monoheteracyclic or polyheterocyclic or fused heterocyclic structure containing from 1-3 of any one of the heteroatoms N, S or O in each heterocyclic ring thereof and each of said rings being from 3-8 membered wherein the substituents are selected from the group consisting of
lower alkyl
lower alkoxy
lower acyl
lower acyloxy
halo such as Cl, Br, I or F
halo lower alkyl
cyano
carbethoxy
lower alkyl thio
amino
nitro
lower alkyl amino
diloweralkyl amino
carboxyl
carbamyl
loweralkylcarbamyl or
dilower alkyl carbamyl.

The term loweralkyl where it appears and is not otherwise defined represents from 1-5 carbon atoms; aryl wherever it appears means a ring of 6 to 10 carbon atoms but preferably phenyl; halo represents Cl, Br, I or F; and loweracyl where it appears refers to a group having from 1 to 5 carbon atoms.

A more preferred aspect of my invention are the novel prodrug forms of formula I wherein $R_1$ is hydrogen or lower alkanoyl having 1 to 4 carbon atoms; $R_2$ is alkyl ($C_{1-10}$) carbon atoms;

akenyl ($C_{2-10}$) cycloalkyl ($C_{4-8}$) aryl ($C_{6-10}$) aralkyl ($C_{6-10}$)

saturated or unsaturated mono- on polyheterocyclic structure containing from 1-3 of any of the heteroatoms N, S or O in each heterocyclic ring thereof and each of said rings being 5 or 6 membered or, substituted saturated or unsaturated mono- or polyheterocyclic structure containing from 1-3 of any of the heteroatoms N, S or O, in each heterocyclic ring thereof and each of said rings being 5 or 6 membered, the substituents being
loweralkyl
loweralkoxy
loweracyl
halo
carbethoxy
amino
carbamyl and
n=1 or 2.

A most preferred aspect of my invention are those novel prodrugs of formula I wherein $R_1$ is acetyl, $R_2$ is t-butyl and methyl and n=1 or 2.

Specific prodrug forms of Ara-A of my invention can be exemplified by the following:
2′,3′,5′-Triacetyl 6-(hydroxymethoxy)methylaminopurine-9-β-D arabinofuranoside;
2″,3″,5″-Triacetyl 6-(3′-acetoxy-2-oxapropyl)aminopurine-9-β-D-arabinofuranoside;
2″,3″,5″-Triacetyl 6-(3′-pivaloxy-2-oxapropyl)aminopurine-9-β-D-arabinofuranoside;
Alternate Preparation of 2″,3″,5″-Triacetyl 6-(3′-acetoxy-2-oxapropyl)aminopurine-9-β-D-arabinofuranoside;
5″-Acetyl 6-(3′-pivaloxy-2-oxapropyl)aminopurine-9-β-D-arabinofuranoside.

The following reaction scheme may be employed to obtain compounds of the present invention.

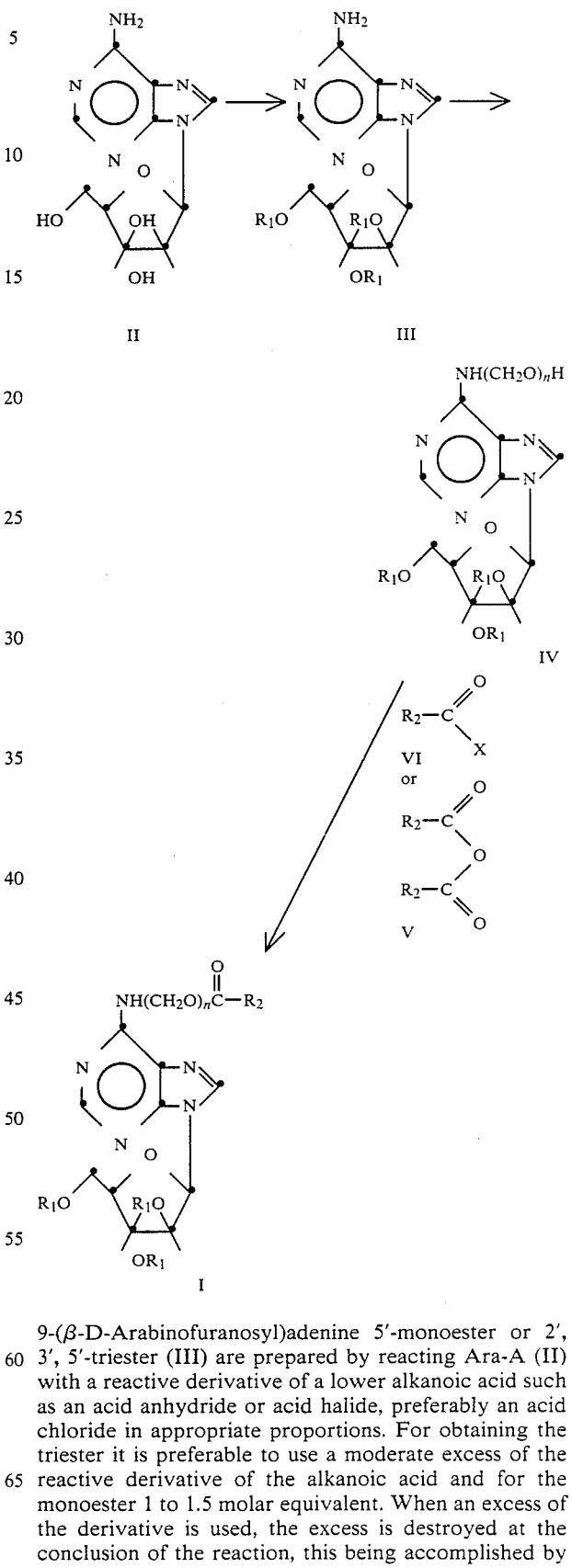

9-(β-D-Arabinofuranosyl)adenine 5′-monoester or 2′, 3′, 5′-triester (III) are prepared by reacting Ara-A (II) with a reactive derivative of a lower alkanoic acid such as an acid anhydride or acid halide, preferably an acid chloride in appropriate proportions. For obtaining the triester it is preferable to use a moderate excess of the reactive derivative of the alkanoic acid and for the monoester 1 to 1.5 molar equivalent. When an excess of the derivative is used, the excess is destroyed at the conclusion of the reaction, this being accomplished by the addition of water or a lower alkanol. The reaction is usually conducted in the presence of a base such as pyridine or triethylamine. The reaction may be carried out in the presence of an excess of the said base as a reaction media, or other suitable medium may be employed such as N,N-dimethylformamide, N,N-dimethylacetanide, dimethylsulfoxide, tetrahydrofuran, dioxane, glyme, or chlorinated solvents such as chloroform or dichloromethane. The reaction medium is maintained at a temperature of 0° to 5°, preferably between 0° and 10°.

(Hydroxymethoxy)methylation of the aforementioned esters is carried out using aqueous formaldehyde at a temperature of 0° to 50°, but preferably between 0° and 10°. The reaction may be carried out in a medium such as water or a water miscible solvent such as dimethylformamide, dimethylacetamide, dimethylsulfoxide, dioxane, hexamethylphosphoramide, tetrahydrofuran, glyme, and the like. In addition to $N^6$- (hydroxymethoxyl)methyl derivative, an N,N'-bis-(hydroxymethoxy)methyl derivative is formed as a side product in the reaction, which is conveniently separated after the following step.

The acylation of the above (hydroxymethoxy)methyl compound to prepare final product I is carried out as described above in the first step using a reactive derivative of a carboxylic acid, such as an anhydride V or acid halide VI. When an excess of the derivative is used, the excess is destroyed at the conclusion of the reaction, this being accomplished by the addition of water or a lower alkanol. The reaction is usually conducted in the presence of a base such as pyridine or triethylamine. The reaction may be carried out in the presence of an excess of the said base as a reaction media, or other suitable medium may be employed such as N,N-dimethylformamide, N,N-dimethylacetanide, dimethylsulfoxide, tetrahydrofuran, dioxane, glyme, or chlorinated solvents such as chloroform or dichloromethane. The reaction medium is maintained at a temperature of 0° to 5°, preferably between 0° and 10°. The $N^6$-(acyloxmethoxy)methyl derivative of 9-($\beta$-D-arabinofuranosyl)adenine esters is then purified by column chromatography on silica gel using a solvent or solvent combination of appropriate polarity.

When $R_2$ and $R_1$ have the same alkenyl groups the derivatives of the present invention may also be prepared by (hydroxymethoxy)methylation of 9-($\beta$-D-arabinofuranosyl)adenine as described above followed by acylation with a reactive derivative of an alkanoic acid.

The prodrug derivatives according to my invention exhibit all the biological and therapeutic activity of their parent antiviral drug species, while at the same time being characterized by enhanced physiological availability and bioavailability. The dose of the prodrug administered will usually be an effective amount which will be the equivalent on a molar basis of the pharmacologically active form produced upon metabolic release of the active parent drug species, to achieve its desired effect.

Dosage levels of the prodrug of my invention of the order from 1 mg to 50 mg per kg of body weight per day are useful in the treatment of the above-indicated conditions. For example, when used in the treatment of herpes, one can administer from about 1 to 50 mg of a prodrug of my invention per kg of body weight per day. Advantageously from about 5 mg to about 30 mg per kg of body weight per daily dosage produces highly effective results.

It will be realized by those skilled in the art that the particular amount of prodrug of my invention which is to be administered to a patient will depend on the severity of the disease, the body weight of the patient and other physical conditions of the patient itself. Those skilled in the art will realize how much of the drug to administer to a patient within the parameters discussed above.

The compounds of the present invention are conveniently administered to warm-blooded animals via conventional topical administration with suitable non-toxic, pharmaceutically acceptable, topical inert carrier vehicles, such as ointments, creams or gels. Also for topical use in addition to ointments, creams and gels, one can use solutions or suspensions and the like containing the prodrug of Ara-A of this invention.

Following are specific examples which illustrate my invention but which should not be held to be limiting thereto.

EXAMPLE 1

2',3',5'-Triacetyl 6-aminopurine-9-$\beta$-D Arabinofuranoside 2 g of 6-aminepurine-9-$\beta$-D-arabinofuranoside (Ara-A) was suspended in 50 ml of pyridine and the reaction mixture was cooled in ice. 25 ml of acetic anhydride was added to the ice cold solution and kept stirring at 0°-4° C. for 20 hrs. Crushed ice (30 g) was added and stirred for ½ hr. to decompose the excess acetylating agent. The volatile solvents were distilled off at room temperature in vacuum. The residue was taken in water (30 ml) and extracted with EtOAc. The EtOAc extract was washed twice with water and then with brine. It was dried over $Na_2SO_4$ and evaporated to a foamy solid weighing 3.7 g. TLC on silica gel using dichloromethane-acetone (1:1) showed the presence of small amounts of $N^6$-acetyl-2',3',5'-triacetyl Ara-A as an impurity. It was chromatographed on 100 g of silica gel. The pure triacetyl Ara-A was eluted by acetone-dichloromethane (1:1) as a white foamy solid, 2.25 g (m.p. 142 on crystallization from EtOH).

EXAMPLE 2

2',3',5'-Triacetyl 6-(hydroxymethoxy) methylaminopurine-9-$\beta$-D arabinofuranoside Triacetyl Ara-A (2.0 g) was dissolved in an ice cold solution of fomalin (20 ml) in water (30 ml) and kept stirred at 0°-4° for 28 hours. The reaction was followed by TLC on silica gel using dichloromethane-acetone (1:1) for developing the chromatogram. Most of the starting material disappeared and two major spots appeared on TLC at the end of 24-28 hours. It was then extracted with dichloromethane and the extract was washed twice with water. The organic extract was dried over $Na_2SO_4$ and evaporated to a thick glue weighing 2.8 g. No purification was attempted for this compound because it was unstable. NMR ($CDCl_3$) 1.96 (3H, s, 5'-OAc), 2.13 and 2.16 (3H each, s, 2' and 3' OAc), 4.2-4.6 (3H, m, 4'-H and 5'-CH$_2$), 5.2-5.7 (6H, m, CH$_2$OCH$_2$-OH and 2'-H and 3'-/H/ ), 6.03 (1H, d, J=4 Hz, 1'-H), 8.11 (1H, aromatic), 8.46 (1H, s, aromatic) and 4.96 (broad, exchangeable with $D_2O$, NH and OH).

EXAMPLE 3

2",3",5"-Triacetyl 6-(3'-acetoxy-2-oxapropyl)aminopurine-9-β-D-arabinofuranoside The above (hydroxymethoxy)methyl derivative (2.8 g) was dissolved in ice cold dry pyridine (25 ml) and acetic anhydride (25 ml) was added with stirring. The reaction mixture was kept stirred at 0°–4° C. for 17 hours. The excess acetylation agent was destroyed by the addition of 25 g of crushed ice. After stirring for 1½ hours at 0°–4° C. the reactants were distilled off in vacuum at room temperature. The residue was diluted with water and washed twice with ether. The ether washings were discarded. The aqueous layer was then extracted with dichloromethane. The dichloromethane extract was washed with water once and then with brine. It was dried over Na$_2$SO$_4$ and evaporated to a foamy solid that weighed 1.1 g. It was chromotographed on silica gel (30 g). Elution with ethyl acetate gave the pure (acetoxymethoxy)methyl derivative 110 mg as a colorless thick glue.

UV$_{max}^{EtOH}$ 263 (ε 14610) m/e 495 (M+),

EXAMPLE 4

2",3",5"-Triacetyl 6-(3'-pivaloxy-2-oxapropyl)aminopurine-9-β-D-arabinofuranoside 6-(Hydroxymethoxy)methylaminopurinearabinoside triacetate prepared as before (1 g) was dissolved in dichloromethane (40 ml) and cooled in ice. Dry pyridine (5 ml) was added with stirring followed by pivalic anhydride (5 ml). It was kept stirred at 0°–4° C. for 48 hours. The excess acylating agent was decomposed by adding 5 ml of methanol to the reaction mixture. After distilling off the pyridine and methyl pivalate at room temperature in vacuum, the residue was suspended in water and extracted with dichloromethane. The dichloromethane extract was washed with water twice and with brine. It was dried with sodium sulfate and evaporated to a light yellow glue (1.54 g). It was chromatographed on silica gel (50 g). Elution with dichloromethane-ethyl acetate (1:1) furnished 152 mg of the pure pivaloxymethoxymethyl derivative as a foamy solid.

EXAMPLE 5

Alternate Preparation of 2",3",5"-Triacetyl 6-(3'-acetoxy-2-oxapropyl)aminopurine-9-β-D-arabinoforanoside Ara-A (200 mg) was taken in dimethyl formamide (5 ml) and stirred with formaline (1 ml) at 0°–4° for 24 hours. The reaction mixture was brought to room temperature and stirred at room temperature for 3 hours. The dimethylformamide and water were evaporated off. The residue was acetylated with acetic anhydride (2 ml) and pyridine at 0°. After destroying the excess acetylating agent by the addition of water, the reaction mixture was worked up by evaporation of the excess acetic acid and pyridine. The residue was extracted with dichloromethane and washed with water and brine. The residue obtained on evaporation was separated on thin layer chromatography plates (silica gel). Development with ethyl acetate-dichloromethane (3:2) followed by elution of the band corresponding to the (acetoxymethoxy)methyl derivative gave the pure compound which was identical in all respects with the one prepared as described before.

EXAMPLE 6

5"-Acetyl 6-(3'-pivaloxy-2-oxapropyl) aminopurine-9-β-D-arabinofuranoside 9-(β-D-Arabinofuranosyl)adenine (2.67 g) was suspended in dimethylformamide (50 ml) and pyridine (50 ml) and cooled in an ice bath. Acetylchloride (0.86 g) was added to the stirred reaction mixture and stirred at 0° to 4° for 22 hours. Water (10 ml) was added to the reaction mixture and stirred for ½ hour. The excess dimethylformamide and pyridine were distilled off in vacuum. The residue was diluted with 25 ml of water and distilled again in vacuum at room temperature. The residue was vacuum dried at 0.001 mm at room temperature for 14 hours. The product was a colorless glass. It was chromatographed on a silica gel column (135 g). Elution with 20% methanol in dichloromethane gave the pure 5"-acetyl Ara-A as a white solid (2.24 g). NMR (CDCl$_3$-DMSO-d$_6$) 2.06 (3H, s, OA$\underline{C}$), 4.2–4.7 (broad), 6.46 (1H, d, J=Hz, 1'-$\underline{H}$), 7.2 (2H, broad s, N$\underline{H_2}$), 8.21 and 8.28 (1H each, s, aromatic). IR (KBr) 3500–3100, 1734, 1693, 1650, 1610, 1254, 1048 cm$^{-1}$.

The above monoacetyl derivative (0.4 g) was dissolved in an ice-cold solution of formalin (2 ml) in water (4 ml) and kept stirred at 0°–4° for 44 hours. It was then diluted with 5 ml of water and extracted with dichloromethane (20 ml, thrice). The dichloromethane layer was discarded. The aqueous layer was evaporated to a thick light yellow oil. It was triturated with dichloromethane and the dichloromethane was pipetted off. This operation was repeated twice. The aqueous layer on vacuum drying gave a glassy solid weighing 250 mg. It was dissolved in dry dimethylformalide (5 ml) and cooled in ice. Dry pyridine (5 ml) was added followed by 0.25 ml of pivalic anhydride. After stirring at 0°–4° for 18 hours, it was maintained at room temperature for 4 hours. The excess pivalic anhydride was decomposed by adding methanol (2 ml), and after stirring for 2 hours, the solvents were evaporated off. The residue was extracted with methylene chloride and the extract washed with water and brine. The residue obtained on evaporation of the solvent was separated on thin layer chromatography plates. The band corresponding to the (pivaloxymethoxy) methyl derivative was scraped out and extracted with EtOAc. Evaporation of EtOAc gave the pure compound as a foam. NMR (CDCl$_3$) 1.21 (9H, s, C($\underline{CH_3}$)$_3$), 2.06 (3H, s, OAc) 5.41 (4H, $\underline{CH_2OCH_2}$), 6.58 (1$\underline{H}$, d, J=4 Hz, 1"=$\underline{H}$), 7.36 (1H, broad t, N$\underline{H}$), 8.21 and 8.28 (1H, each, s, aromatic).

EXAMPLE 7

Composition of a typical cream formulation prepared by known methods to those skilled in the art is given below:

| | |
|---|---|
| Cetyl alcohol | 3.0% |
| Stearyl alcohol | 10.0% |
| Arlacel 83 | 15.0% |
| Sorbitan sesquioleate | 3.0% |
| Petrolatum | 13.0% |
| Drug + vehicle | 1.0% |
| Amerchol L-101 | 5.0% |
| propylene glycol | 5.0% |
| sorbilot solution 70% | 5.0% |
| Tween 60 | 5.0% |
| water, deionized | 35.0% |
| preservatives | q.s. (small unmeasurable amount) |
| perfume | q.s. (small |

|                     |
| ------------------- |
| -continued          |
| unmeasurable amount) |

What is claimed is:

1. A compound of the formula:

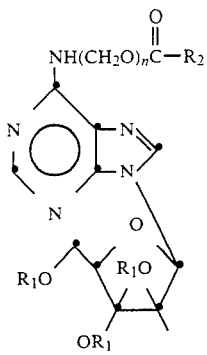

wherein n is 1 or 2;

$R_1$ is independently H or lower alkanoyl having from 1 to 4 carbon atoms;

$R_2$ is selected from the group consisting of:
  (a) straight or branched chain alkyl having from 1–20 carbon atoms;
  (b) aryl having from 6–10 carbon atoms;
  (c) cycloalkyl having from 3–8 carbon atoms;
  (d) alkenyl having from 2–20 carbon atoms;
  (e) cycloalkenyl having from 4–8 carbon atoms;
  (f) alkynyl having from 2 to 20 carbon atoms;
  (g) aralkyl having from 7–26 carbon atoms;
  (h) aralkenyl having from 7–26 carbon atoms;
  (i) lower acyloxy alkyl having from 2–20 carbon atoms;
  (j) carboxyalkyl having from 2–20 carbon atoms.

2. A compound of the formula:

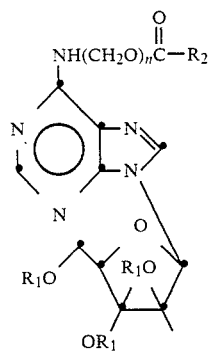

wherein $R_1$ is hydrogen or lower alkanoyl having 1 to 4 carbon atoms;

$R_2$ is alkyl ($C_{1-10}$)
  alkenyl ($C_{2-10}$)
  cycloalkyl ($C_{4-8}$)
  aryl ($C_{6-10}$)
  aralkyl ($C_{6-10}$) and n = 1 or 2.

3. A compound of the formula:

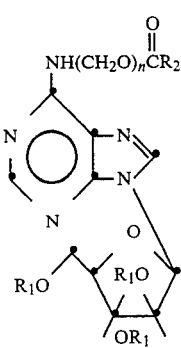

wherein $R_1$ is independently H or acetyl;

$R_2$ is methyl or t-butyl;

n = 1 or 2.

4. 2′,3′,5′-triacetyl 6-(hydroxymethoxy)methylamino-purine-9-β-D arabinofuranoside.

5. The compound of claim 1 which is 2″,3″,5″-triacetyl 6-(3′-acetoxy-2-oxapropyl) aminopurine-9-β-D-arabinofuranoside.

6. The compound of claim 1 which is 2″,3″,5″-triacetyl 6-(3′-pivaloxy-2-oxapropyl)aminopurine-9-β-D-arabinofuranoside.

7. The compound of claim 1 which is 5″-acetyl 6-(3′-pivaloxy-2-oxapropyl)aminopurine-9-β-D-arabinofuranoside.

8. An antimetabolite against herpes virus pharmaceutical composition for topical application comprising an anti-herpes virus effective amount of an active drug of the formula:

Formula I wherein n is 1 or 2;

$R_1$ is independently H or lower alkanoyl having from 1 to 4 carbon atoms;

$R_2$ is selected from the group consisting of:
  (a) straight or branched chain alkyl having from 1–20 carbon atoms;
  (b) aryl having from 6–10 carbon atoms;
  (c) cycloalkyl having from 3–8 carbon atoms;
  (d) alkenyl having from 2–20 carbon atoms;
  (e) cycloalkenyl having from 4–8 carbon atoms;
  (f) alkynyl having from 2 to 20 carbon atoms;
  (g) aralkyl having from 7–26 carbon atoms;
  (h) aralkenyl having from 7–26 carbon atoms;
  (i) lower acyloxy alkyl having from 2–20 carbon atoms;
  (j) carboxyalkyl having from 2–20 carbon atoms.

9. A method of treating herpes infection which comprises administering to a patient in need of such treatment 1 mg. to 50 mg. per kg. of body weight per day of a compound of the formula:

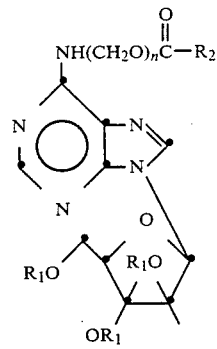

wherein
n is 1 or 2;
$R_1$ is independently H or lower alkanoyl having from 1 to 4 carbon atoms;
$R_2$ is selected from the group consisting of:
  (a) straight or branched chain alkyl having from 1–20 carbon atoms;
  (b) aryl having from 6–10 carbon atoms;
  (c) cycloalkyl having from 3–8 carbon atoms;
  (d) alkenyl having from 2–20 carbon atoms;
  (e) cycloalkenyl having from 4–8 carbon atoms;
  (f) alkynyl having from 2 to 20 carbon atoms;
  (g) aralkyl having from 7–26 carbon atoms;
  (h) aralkenyl having from 7–26 carbon atoms;
  (i) lower acyloxy alkyl having from 2–20 carbon atoms;
  (j) carboxyalkyl having from 2–20 carbon atoms.

* * * * *